United States Patent [19]

Archibald et al.

[11] 4,357,333
[45] Nov. 2, 1982

[54] N-SUBSTITUTED-2-(8-HALO AND-TRIFLUOROMETHYL-4-QUINOLYLAMINO)BENZAMIDES AND ANALGESIC USE THEREOF

[75] Inventors: John L. Archibald, Windsor; John T. A. Boyle, Maidenhead, both of England

[73] Assignee: John Wyeth & Brother Limited, Maidenhead, England

[21] Appl. No.: 177,305

[22] Filed: Aug. 11, 1980

Related U.S. Application Data

[63] Continuation of Ser. No. 939,101, Sep. 1, 1978, abandoned.

[30] Foreign Application Priority Data

Sep. 14, 1977 [GB] United Kingdom ............... 38264/77

[51] Int. Cl.³ ................. C07D 215/46; C07D 403/12; A61K 31/47
[52] U.S. Cl. ..................................... 424/258; 546/161
[58] Field of Search ........................ 546/161; 424/258

[56] References Cited

U.S. PATENT DOCUMENTS 3,174,972  3/1965  Allais et al. .......................... 424/258
3,875,165  4/1975  Archibald et al. .................. 424/258
4,025,629  5/1977  Coverdale ............................ 424/258

Primary Examiner—David B. Springer
Attorney, Agent, or Firm—Arthur E. Wilfond

[57] ABSTRACT

The disclosure describes new 4-aminoquinoline derivatives of general formula

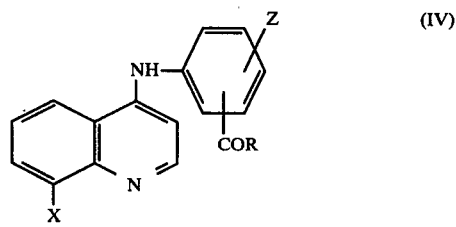

and their pharmaceutically acceptable acid addition salts, where X is trifluoromethyl or halogen, Z is hydrogen or a defined substituent and R is a group having one of the formulae

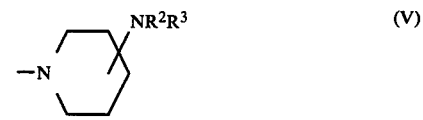

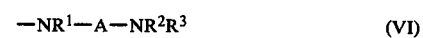

and

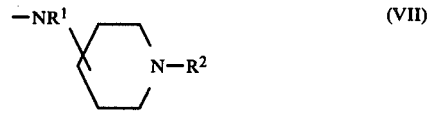

where $R^1$ is hydrogen or lower alkyl, $R^2$ is lower alkyl, $R^3$ is lower alkyl and A is lower alkylene. The new 4-aminoquinoline derivatives show analgesic activity and, in some cases, anti-inflammatory activity.

13 Claims, No Drawings

N-SUBSTITUTED-2-(8-HALO AND TRIFLUOROMETHYL-4-QUINOLYLAMINO)BENZAMIDES AND ANALGESIC USE THEREOF

This is a continuation, of application Ser. No. 939,101, filed Sept. 1, 1978, now abandoned.

The invention relates to 4-aminoquinoline derivatives, a process for their preparation and pharmaceutical compositions containing them.

British Patent Specification No. 1416872 discloses 4-aminoquinoline derivatives having the general formula

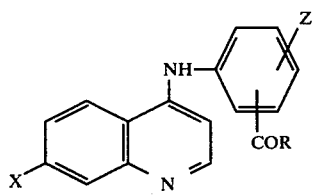

and their pharmaceutically acceptable acid addition salts, where X is halogen or trifluoromethyl, Z is hydrogen, halogen, trifluoromethyl, lower alkyl, lower alkoxy, hydroxy, nitro, amino or mono- or di- alkyl substituted amino and R represents a group having the formula

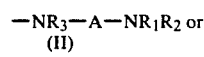

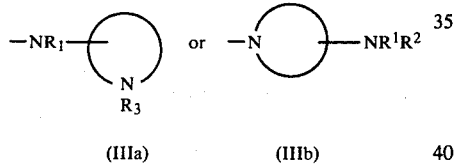

wherein
(a) in formula II A represents a chain of 1 to 5 methylene groups, which may be substituted by one or more alkyl groups;
(b) in formula IIIa and IIIb the ring denotes a piperidine or pyrrolidine ring that may be substituted by one or more alkyl groups or by a divalent aliphatic chain substituting two different ring members of the piperidine or pyrrolidine ring;
(c) $R_1$ represents a hydrogen atom, an alkyl group, an aralkyl group, an acyl group or an aryl group, $R_2$ represents a hydrogen atom, an alkyl group, an aralkyl group or an acyl group, or, in formula II or IIIb, $R_1$ and $R_2$ may together form the diacyl residue of a dicarboxylic acid or $R_1$ and $R_2$ may together form a divalent radical such that $R_1R_2NH$ is a secondary cyclic amine with 5 to 7 ring atoms; and
(d) in formula II $R_3$ represents lower alkyl and in formula IIIa $R_3$ represents a hydrogen atom, an alkyl group, an aralkyl group, or an alkyl group substituted by a heterocyclic group, or an aliphatic chain joining the nitrogen atom member to another ring member of the ring in formula IIIa.

It will be observed that in formula I the substituent X is at the 7-position of the quinoline ring. The 4-aminoquinoline derivatives of the said patent specification are disclosed as anti-malarial agents. We have now found that some new related compounds where the substituent X is at the 8-position instead show analgesic activity, a utility which is not disclosed in said patent specification.

The invention provides new compounds having the general formula

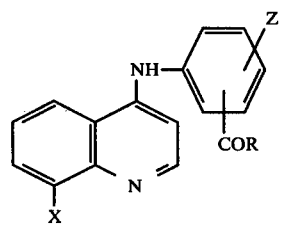

and their pharmaceutically acceptable acid addition salts, wherein X is trifluoromethyl or halogen, Z is hydrogen, halogen, lower alkyl, lower alkoxy, nitro, di(lower alkyl) amino or trifluoromethyl and R is a group having one of the formulae

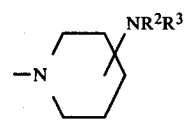

and

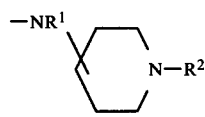

wherein $R^1$ is hydrogen or lower alkyl, $R^2$ is lower alkyl, $R^3$ is lower alkyl and A is lower alkylene.

By the term "lower" as used in connection with such groups as alkyl, alkoxy and alkylene, there is meant that the group contains up to 6 carbon atoms, preferably up to 4 carbon atoms.

It will be apparent to those skiled in the art that the above definition of R includes moieties possessing an asymmetric carbon atom, for instance, in the cases where A represents a branched lower alkylene group and where R represents a group of the formula

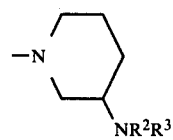

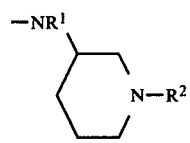

It is to be understood that general formula I is intended to encompass both enantiomers where the compound contains an asymmetric carbon atom and also mixtures of the enantiomers, for instance, a racemic mixture of enantiomers. General methods are recorded in the literature for the resolution of enantiomers.

In the compounds of formula IV, X preferably represents trifluoromethyl but may also represent halogen, for instance, chlorine or bromine. Illustrative meanings of Z include hydrogen, chlorine, bromine, methyl, ethyl, propyl, butyl, methoxy, ethoxy, propoxy, butoxy, nitro, dimethylamino, methylethylamino, diethylamino and trifluoromethyl. Z is preferably hydrogen. In formula IV the group —COR may substitute any ring position (o-, m- or p-position) relative to the 8-(trifluoromethyl or halogen)-4-quinolylamino substituent but preferably substitutes the o-position. $R^1$ represents hydrogen or lower alkyl, for instance, methyl, ethyl, propyl or butyl. $R^1$ preferably represents lower alkyl in formula VI and hydrogen is formula VII. $R^2$ and $R^3$ represent the same or different lower alkyl groups, for instance, methyl, ethyl, propyl and butyl. In formula VI A represents lower alkylene, for instance, straight chain lower alkylene such as methylene, dimethylene, trimethylene, tetramethylene or pentamethylene or branched chain lower alkylene, for example -CH(CH$_3$)-CH$_2$- or -CH$_2$-CH(CH$_3$)-CH$_2$-. R preferably represents a group of formula VI or VII. R is most preferably (1-lower alkyl-3-piperidyl)amino, that is, a group of formula VIIa where $R^1$ is hydrogen, or a group of formula VI where $R^1$ is lower alkyl.

Examples of acid addition salts are those formed from inorganic and organic acids and include the sulphate, hydrochloride, hydrobromide, hydroiodide, nitrate, phosphate, sulphonates (for example, the methanesulphonate and p-toluenesulphonate), acetate, maleate, fumarate, tartrate, malonate, citrate and formate.

Illustrative examples of the compounds of the invention include N-(1-ethyl-3-piperidyl)-2-(8-trifluoromethyl-4-quinolylamino)benzamide; N-(2-diethylaminoethyl)-N-ethyl-2-(8-trifluoromethyl-4-quinolylamino)-benzamide; N-(1-ethyl-3-piperidyl)-4-(8-trifluoromethyl-4-quinolylamino)benzamide; N-(2-diethylaminoethyl)-N-ethyl-4-(8-trifluoromethyl-4-quinolylamino)-benzamide; N-(1-ethyl-4-piperidyl)-2-(8-trifluoromethyl-4-quinolylamino)benzamide; 4-dimethylamino-1-[2-(8-trifluoromethyl-4-quinolylamino)benzoyl]piperidine; 2-(8-chloro-4-quinolylamino)-N-(1-ethyl-3-piperidyl)-benzamide; 2-(8-chloro-4-quinolylamino)-N-(2-diethylaminoethyl)-N-ethylbenzamide and their pharmaceutically acceptable acid addition salts.

The compounds of the invention may be made by building the compound by known reactions. In particular, the amide linkage shown in formula IV as -COR may be formed by acylation of an appropriate amine or an appropriate substitued aniline may be converted into a secondary amine by introducing the 8-(trifluoromethyl or halo)-4-quinolyl radical in known manner.

The invention provides a process for the preparation of a compound having formula IV or a pharmaceutically acceptable acid addition salt thereof wherein
  (a) an amine having formula RH (where R is as defined above in connection with formula IV) or a corresponsing compound with an activated amino group is acylated with a compound having the formula

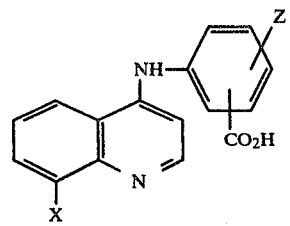

(where X and Z are as defined above in connection with formula IV) or a reactive derivative thereof; or
  (b) a substituted aniline having the formula

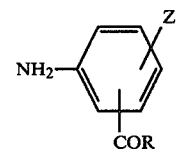

(where Z and R are as defined above in connection with formula IV) is reacted with a compound having the formula

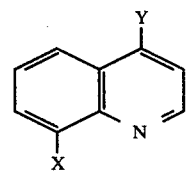

(where X is as defined above in connection with formula IV and Y represents a group or atom replaceable by nucleophilic attack by the substituted aniline of formula IX). Y is, for instance, an iodine, bromine or chlorine atom or an organosulphonyloxy group, for instance, p-toluenesulphonyloxy. Where necessary or desired, the process may also include conversion of the free base form of a compound having formula IV into a pharmaceutically suitable acid addition salt thereof or conversion of an acid addition salt of a compound having formula IV into the free base form. The starting materials of formula RH and formulae VIII, IX and X are known compounds or, where new, are accessible by conventional methods.

The acylation method may be carried out by reacting the acid having the formula VIII with the amine having formula RH in the presence of a condensing agent, for example a carbodiimide. Alternatively the acid having formula VIII may be reacted with a compound in which an amino function has been activated, for example, by forming the phosphazo derivative. The reactive acylating derivatives of the compound having formula VIII may be employed, for example, active esters, acyl halides, simple or mixed anhydrides and the acid azide. The acid halides, particularly the acid chloride, are especially suitable. The acylation may be performed according to regular procedures and the acylation product may be recovered from the reaction mixture by standard isolation procedures.

Compounds having the formula IX are accessible in standard manner, for example, by acylation of a compound of formula RH (where R is as defined above in connection with formula IV) with an acylating derivative of a nitrobenzoic acid or (protected amino)benzoic acid and subsequent reduction of the nitro group or removal of the protecting group. The reaction of the primary amine IX with the compound of formula X may be carried out in conventional manner for amination of 4-substituted quinolines. The reaction products may be recovered from the reaction mixtures by standard isolation techniques.

The compounds of the present invention may be isolated in free base form or as an acid addition salt. Acid addition salts may be converted into the free bases in conventional manner. The free bases may be converted into acid addition salts in conventional manner, for instance, by adding ethereal hydrogen chloride to a solution of the free base where a hydrochloride salt is desired.

The compounds having formula IV and their pharmaceutically acceptable acid addition salts are indicated for pharmacological usage. In particular they show analgesic activity and also, in some cases, anti-inflammatory activity when tested on mammals. The compounds may be tested for activity in the following tests:

A. Mouse Writhing Test For Analgesic Activity
Test Object: Female Tuck Mice
Procedure:

Groups of five female Tuck mice are dosed orally with varying concentrations of the test compound (or with 0.9% saline in the case of the controls) at fifteen minute intervals. Thirty minutes afterwards each group is dosed intra-peritoneally with 60 mg/kg of acetic acid, administered as 10 ml of acetic acid solution (concentration 6 mg/ml) per kg body weight. The animals are placed under separate beakers to facilitate observation and the number of writhes by each animal for the period 5-15 minutes after acetic acid challenge is recorded. The $ED_{50}$ is the dose of test compound causing a 50% reduction in the number of writhes compared with the controls.

B. Adjuvant Arthritis Test for Anti-Inflammatory Activity
Test Object: Male Lewis Rats
Procedure:

Polyarthritis is induced in male Lewis strain rats (150-200 gms) by the injection of a suspension of tubercle bacilli in mineral oil in the subplantar tissue of the right hind paw. Drug therapy is either begun on the day of antigen or can be started after appearance of an established arthritic syndrome (14 days). Compounds are administered daily in the form of a fine suspension by stomach tube. Body weights, left and injected right paw volumes and occurrence of arthritic nodules on the ears, tail and front paws are determined at frequent intervals over a 14 to 21 day period. All animals are then autopsied and stress organ weights, hematology, histopathology and biochemical studies on blood proteins are done. Active compounds will either prevent or reverse the joint swelling and associated sequella of polyarthritis.

The test results for the products of Examples 1 to 6 herein are given in the following table.

| Example No. | Procedure A | Procedure B [Doses administered p.o.] |
|---|---|---|
| 1 | $ED_{50}$ = 16 mg/kg | Very good activity at 150 mg/kg. |
| 2 | $ED_{50}$ = 43 mg/kg | Active at 50 mg/kg in the uninjected paw |
| 3(b) | $ED_{50}$ = 191 mg/kg | Inactive |
| 4 | $ED_{50}$ = 200 mg/kg | Active at 100 mg/kg |
| 5 | $ED_{50}$ = 89 mg/kg | Inactive |
| 6 | Not Tested | Active at 100 mg/kg |

The invention also includes pharmaceutical compositions containing as active ingredients a compound of formula IV or a pharmaceutically acceptable acid addition salt thereof. In addition to the active ingredient, said compositions also contain a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium, carbonate, magnesium stearate, talc, sugar, lactose, pectin, dextrin, starch, gelatin, tragacanth, methyl cellulose, sodium carboxymethyl cellulose; a low melting wax, and cocoa butter. The term "composition" is intended to include the formation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile or suspensions can be utilised by intramuscular, intraperitoneal or subcutaneous injection. In many instances a compound is orally active and can be administered orally either in liquid or solid composition form.

The invention is illustrated by the following Examples:

EXAMPLE 1

N-(1-Ethyl-3-piperidyl)-2-(8-trifluoromethyl-4-quinolylamino)benzamide 11.5 Grams (0.0285 Mole) of 2-(8-trifluoromethyl-4-quinolylamino)benzoic acid hydrochloride dihydrate were refluxed in 80 milliliters of thionyl chloride for half an hour. A yellow solid precipitated. The thionyl chloride was evaporated off. The resulting acid chloride hydrochloride was added in portions with stirring to a cooled mixture of 3.84 grams (0.03 moles) of 3-amino-1-ethylpiperidine in 100 milliliters of chloroform and 31.8 grams (0.3 mole) of sodium carbonate in 100 milliliters of water. The mixture was stirred for one hour and allowed to stand overnight. The chloroform layer was separated and dried and the chloroform evaporated to give a nearly colourless solid. Trituration with ether gave a colourless solid which was recrystallized from methanol to give 7.9 grams (63% yield) of title compound, melting point 212° to 213° C.

Analysis: Found: C, 65.6%; H, 5.81%; N, 12.4%. $C_{24}H_{25}F_3N_4O$ requires: C, 65.2%; H, 5.69%; N, 12.7%.

EXAMPLE 2

N-(2-diethylaminoethyl)-N-ethyl-2-(8-trifluoromethyl-4-quinolylamino)benzamide 12.1 Grams (0.03 mole) of 2-(8-trifluoromethyl-4-quinolylamino)benzoic acid hydrochloride dihydrate were refluxed in 80 milliliters of thionyl chloride for half an hour. A yellow solid precipitated. The thionyl chloride was evaporated off and 50 milliliters of benzene were added and evaporated. The resulting acid chloride hydrochloride was added in portions with stirring to a cooled mixture of 4.32 grams (0.03 mole) of N,N,N'-triethylethylenediamine in 80 milliliters of chloroform and 31.8 grams (0.3 mole) of sodium carbonate in 100 milliliters of water. The mixture was stirred for one hour, and allowed to stand overnight. The chloroform layer was separated and dried and the chloroform evaporated to give an oil, which could not be solidified. The oil was dissolved in ether and purified by chromatography on an alumina (type H) column. Elution with ether/chloroform (50:50) gave a pale yellow oil which was kept under vacuum for four days when it gradually solidified to give 6.35 grams (46% yield) of title compound of melting point 112°–113° C.

Analysis: Found: C, 65.4%; H, 6.51%; N, 12.3% $C_{25}H_{29}F_3N_4O$ requires C, 65.5%; H, 6.37%, N, 12.2%.

EXAMPLE 3

(a) 4-(8-Trifluoromethyl-4-quinolylamino)benzoic acid 23.16 Grams (0.1 mole) of 4-chloro-8-trifluoromethyl quinoline were dissolved in 22 milliliters of concentrated hydrochloric acid and 150 milliliters of water and the solution was added in a stream to a vigorously stirred solution of 13.7 grams (0.1 mole) of p-aminobenzoic acid in 150 milliliters of water at 60° C. The mixture was heated at 90° C. for 2 hours, cooled, and the solid collected and recrystallized from ethanol to give 32.1 grams (83%) of the title compound as the hydrochloride monohydrate, melting point 262°–265° C.(d).

Analysis: Found: C, 53.2%; H, 3.7%; N, 6.95%. $C_{17}H_{14}ClF_3N_2O_3$ requires C, 52.8%; H, 3.65; N, 7.24%.

(b) N-(1-Ethyl-3-piperidyl)-4-(8-trifluoromethyl-4-quinolylamino)benzamide 11.6 Grams (0.03 mole) of 4-(8-trifluoromethyl-4-quinolylamino)benzoic acid hydrochloride monohydrate were refluxed in thionyl chloride containing a few drops of dimethyl formamide for one hour. The thionyl chloride was evaporated and 50 milliliters of benzene were added and evaporated. The resulting acid chloride hydrochloride was added in portions with stirring to a cooled mixture of 3.84 grams (0.03 mole) of 3-amino-1-ethylpiperidine in 80 milliliters of chloroform and 31.8 grams (0.3 mole) of sodium carbonate in 100 milliliters of water. The product began to precipitate almost at once, and the mixture was stirred vigorously for two hours, and allowed to stand overnight. Filtration gave a solid which was stirred in water, collected and dried. The resulting solid was dissolved in an ethanol:chloroform mixture and chromatographed on an alumine column made up in chloroform. Elution with chloroform gave 4.9 grams (37%) of title compound as a pale yellow solid, melting point 177°–178° C.

Analysis: Found: C, 64.9%; H, 5.92%; N, 12.4%. $C_{24}H_{25}F_3N_4O$ requires C, 65.2%; H, 5.69%; N, 12.7%.

EXAMPLE 4

N-(2-Diethylaminoethyl)-N-ethyl-4-(8-trifluoromethyl-4-quinolylamino)benzamide 11.6 Grams (0.03 mole) of 4-(8-trifluoromethyl-4-quinolylamino)benzoic acid hydrochloride monohydrate were refluxed in 80 milliliters of thionyl chloride containing two drops of dimethyl formamide for 1½ hours. The thionyl chloride was evaporated off and 50 milliliters of benzene were added and evaporated. The resulting acid chloride hydrochloride was added in portions with stirring to a cooled mixture of 4.32 grams (0.03 mole) of N,N,N'-triethyl ethylenediamine in 80 milliliters of chloroform and 31.8 grams (0.3 mole) of sodium carbonate in 100 milliliters of water. The mixture was stirred for one hour, and allowed to stand overnight. The chloroform layer was separated and dried and the chloroform evaporated to give a gummy solid, which was largely taken up in ether. On concentration of this solution a colourless solid crystallised out, which was collected to give 8.8 grams (63% yield) of N-(2-diethylaminoethyl)-N-ethyl-4-(8-trifluoromethyl-4-quinolylamino)benzamide quarter hydrate, m.p. 151°–152° C.

Analysis: Found: C, 64.9%; H, 6.49%; N, 11.7%. $C_{25}H_{29}F_3N_4O \cdot \frac{1}{4} H_2O$ requires C, 64.9%; H, 6.42%; N, 12.1%.

EXAMPLE 5

N-(1-Ethyl-4-piperidyl)-2-(8-trifluoromethyl-4-quinolylamino)benzamide 12.92 Grams (0.035 moles) of 2-[8-trifluoromethyl-4-quinolylamino]benzoic acid hydrochloride hemihydrate were refluxed in 160 milliliters of thionyl chloride for 1 hour. The thionyl chloride was evaporated to give the acid chloride hydrochloride as a yellow solid. The acid chloride hydrochloride was added in small portions to a mixture cooled at 0° C. of 4.5 grams (0.035 moles) of 4-amino-1-ethylpiperidine in 100 milliliters of chloroform and 36.1 grams (0.26 moles) of potassium carbonate in 100 milliliters of water. After dissolution of the acid chloride, the reaction mixture was allowed to warm to room temperature and left standing overnight. A solid was filtered off and re-crystallized from a large volume (100 milliliters per gram of solid) of methanol to give 2.18 grams of the title compound as a colourless solid of melting point 159°–162° C. (with decomposition).

Analysis: Found: C, 64.9%; H, 5.69%; N, 12.4%. $C_{24}H_{25}F_3N_4O$ requires C, 65.2%; H, 5.69%; N, 12.7%.

The chloroform/aqueous layers were separated and the aqueous layer was extracted with chloroform. The chloroform portions were combined, washed with water, dried (magnesium sulphate) and evaporated to give a solid. The solid was added to 95% ethanol and the mixture was boiled. Filtration gave 1.23 grams of the title compound as a colourless solid of melting point 159°–162° C. (with decomposition).

Analysis: Found: C, 65.2%; H, 5.81%; N, 12.4%. $C_{24}H_{25}F_3N_4O$ requires C, 65.2%; H, 5.69%; N, 12.7%.

EXAMPLE 6

4-Dimethylamino-1-[2-(8-trifluoro-4-quinolylamino)-benzoyl]piperidine 8.3 Grams (0.023 mole) of 2-[8-trifluoromethyl-4-quinolylamino]benzoic acid hydrochloride were refluxed in 100 milliliters of thionyl chloride for 0.5 hour. The thionyl chloride was evaporated to give the acid chloride hydrochloride as a light yellow solid. To a cooled solution of 4.5 grams (0.023 mole) of 4-[dimethylamino]piperidine dihydrochloride in 100 milliliters of chloroform with 100 milliliters of water and 17.6 grams (0.23 moles) of potassium carbonate was added the acid chloride hydrochloride in small portions. After dissolution of the acid chloride the reaction was allowed to warm to room temperature and stirred for 3 hours. The layers were separated and the aqueous layer was extracted with chloroform. The chloroform portions were combined, washed with water, dried (MgSO₄) and evaporated to give a sticky solid. Methanol was added and re-evaporated to give a light yellow solid. This solid was recrystallised from a large volume of acetone to give 5.43 grams (51% yield) of 4-dimethylamino-1-[2-(8-trifluoromethyl-4-quinolyl)-benzoyl]piperidine as a colourless solid, melting point 174°–176° C.

Analysis: Found: C, 65.2%; H, 5.75%; N, 12.8%. $C_{24}H_{25}F_3N_4O$ requires C, 65.2%; H, 5.75%; N, 12.7%. A second crop amounting to 1.20 grams (12% yield) was obtained.

Analysis: Found: C, 64.8%; H, 5.77%; N, 12.6%. $C_{24}H_{25}F_3N_4O$ requires C, 65.2%; H, 5.75%; N, 12.7%.

EXAMPLE 7

N-(1-Ethyl-3-piperidyl)-4-trifluoromethyl-2-(8-trifluoromethyl-4-quinolylamino)benzamide 4-Trifluoromethyl-2-(8-trifluoromethyl-4-quinolylamino)benzoyl chloride hydrochloride prepared by reaction of 4-chloro-8-trifluoromethyl quinoline with 2-amino-4-trifluoromethylbenzoic acid and treatment of the reaction product with thionyl chloride, is reacted with 3-amino-1-ethylpiperidine to form the title compound.

EXAMPLE 8

N-(1-Butyl-3-piperidyl)-4-chloro-2-(8-trifluoromethyl-4-quinolylamino)benzamide

4-Chloromethyl-2-(8-trifluoromethyl-4-quinolylamino)benzoyl chloride hydrochloride prepared by reaction of 4-chloro-8-trifluoromethylquinoline with 2-amino-4-chlorobenzoic acid and treatment of the reaction product with thionyl chloride, is reacted with 3-amino-1-butylpiperidine to form the title compound.

EXAMPLE 9

2-Dimethylamino-N-(1-ethyl-3-piperidyl)-4-(8-trifluoromethyl-4-quinolylamino)benzamide The title compound is prepared in a manner similar to Example 3 using 4-amino-2-(dimethylamino)benzoic acid instead of p-aminobenzoic acid.

EXAMPLE 10

N-(1-Ethyl-3-piperidyl)-3-methoxy-4-(8-trifluoromethyl-4-quinolylamino)benzamide The title compound is prepared in a manner similar to Example 3 using 4-amino-3-methoxybenzoic acid instead of p-aminobenzoic acid.

EXAMPLE 11

3-Dipropylamino-1-[5-iodo-2-(8-trifluoro-4-quinolylamino)benzoyl]-piperidine

5-Iodo-2-(8-trifluoromethyl-4-quinolylamino)benzoyl chloride hydrochloride prepared by reaction of 4-chloro-8-trifluoromethylquinoline with 2-amino-5-iodobenzoic acid and treatment of the reaction product with thionyl chloride, is reacted with 3-dipropylaminopiperidine to afford the title compound.

EXAMPLE 12

N-(4-Dipropylaminobutyl)-3-methyl-N-propyl-2-(8-trifluoromethyl-4-quinolylamino)benzamide 3-Methyl-2-(8-trifluoromethyl-4-quinolylamino)-benzoyl chloride hydrochloride prepared by the reaction of 4-chloro-8-trifluoromethylquinoline with 2-amino-3-methylbenzoic acid and treatment of the reaction product with thionyl chloride, is reacted with 1-dipropylamino-4-propylaminobutane to afford the title compound.

EXAMPLE 13

N-(1-Methyl-4-piperidyl)-4-nitro-2-(8-trifluoromethyl-4-quinolylamino)benzamide

4-Nitro-2-(8-trifluoromethyl-4-quinolylamino)benzoyl chloride hydrochloride prepared by the reaction of 4-chloro-8-trifluoromethylquinoline with 2-amino-4-nitrobenzoic acid and treatment of the reaction product with thionyl chloride, is reacted with 4-amino-1-methylpiperidine to afford the title compound.

EXAMPLE 14

N-(1-Ethyl-3-piperidyl)-4-(8-trifluoromethyl-4-quinolylamino)benzamide

4-Aminobenzoyl chloride hydrochloride is reacted with 3-amino-1-ethylpiperidine to afford 4-amino-N-(1-ethyl-3-piperidyl)benzamide which is reacted with 4-chloro-8-trifluoromethylquinoline to afford the title compound, melting point 177°–178° C.

EXAMPLE 15

2-(8-Chloro-4-quinolylamino)-N-(1-ethyl-3-piperidyl)-benzamide 16.76 Grams (0.05 mole) of 2-(8-chloro-4-quinolylamino)benzoic acid in 150 milliliters of thionyl chloride were refluxed for half an hour. The thionyl chloride was evaporated to give the acid chloride as a yellow solid. To a solution of 6.41 grams (0.05 mole) of 3-amino-1-ethylpiperidine in 200 milliliters of chloroform, 52.99 grams (0.5 mole) of sodium carbonate and 175 milliliters of water at 0° C. there was added the acid chloride in small portions. Upon dissolution of the acid chloride, the reaction mixture was allowed to warm to room temperature and left standing overnight. The layers were separated, the aqueous layer was extracted with chloroform and the chloroform solutions were combined, washed with water, dried (magnesium sulphate) and evaporated to give a yellow sticky solid, which was titurated with anhydrous ether to give 14.82 grams (61% yield) of 2-(8-chloro-4-quinolylamino)-N-(1-ethyl-3piperidyl)benzamide as a light yellow solid, melting point 173°–75° C.

Analysis: Found: C, 67.2%; H, 6.22%; N, b 13.5% $C_{23}H_{25}ClN_4O$ requires C, 67.6%; H, 6.16%; N, 13.7%.

EXAMPLE 16

2-(8-Chloro-4-quinolylamino)-N-(2-diethylamino)-N-ethylbenzamide 16.76 Grams (0.05 mole) of 2-(8-chloro-4-quinolylamino) benzoic acid hydrochloride in 150 milliliters of thionyl chloride were refluxed for half an hour. The thionyl chloride was evaporated to give the acid chloride as a yellow solid. To a cooled solution of 7.21 grams (0.05 mole) of N,N,N'-triethyl-ethylene diamine in 200 milliliters of chloroform, 52.99 grams (0.5 mole) of sodium carbonate and 175 milliliters of water, there was added the acid chloride in portions. After dissolution of the acid chloride, the reaction mixture was allowed to warm to room temperature and left standing overnight.

The layers were separated, the aqueous layer was extracted with chloroform and the chloroform solutions were combined, washed with water, dried (magnesium sulphate) and evaporated to give an oil. The oil was purified by chromatography using an alumina column (type UG). A clean oil was obtained as the first fraction by elution with ether/chloroform (1:4 by volume). The oil was dissolved in anhydrous ether and ethereal hydrogen chloride was added to give 10.56 grams (42% yield) of 2-(8-chloro-4-quinolylamino)-N-(2-diethylaminoethyl)-N-ethylbenzamide dihydrochloride dihydrate as a pale yellow solid, melting point 195°–198° C. Analysis: Found: C, 53.7%; H, 6.44%; N, 10.2%. $C_{24}H_{31}Cl_3N_4O \cdot 2H_2O$ requires C, 54.0%; H, 6.71%; N, 10.5%.

We claim:

1. A compound having the formula

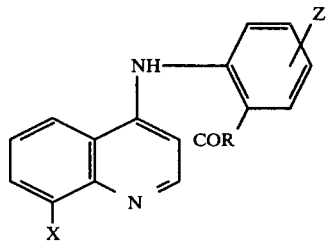

or a pharmaceutically acceptable acid addition salt thereof, wherein X is selected from trifluoromethyl and halogen, Z is selected from hydrogen, halogen, lower alkyl, lower alkoxy, nitro, di(lower alkyl) amino and trifluoromethyl and R is selected from the groups having the formulae $$-NR^1-A-NR^2R^3 \quad (VI)$$

and

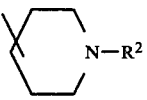

wherein $R^1$ is selected from hydrogen and lower alkyl, $R^2$ is lower alkyl, $R^3$ is lower alkyl and A is lower alkylene.

2. A compound as defined in claim 1, wherein Z is hydrogen.

3. A compound as defined in claim 1, wherein R is selected from (1-lower alkyl-3-piperidyl)amino and a group of formula VI, wherein $R^1$ is lower alkyl.

4. A compound as defined in claim 1, wherein X is trifluoromethyl.

5. A compound as defined in claim 1, which is N-(1-ethyl-3-piperidyl)-2-(8-trifluoromethyl-4-quinolylamino)benzamide or a pharmaceutically acceptable acid addition salt thereof.

6. A compound as defined in claim 1, which is N-(2-diethylaminoethyl)-N-ethyl-2-(8-trifluoromethyl-4-quinolylamino)benzamide or a pharmaceutically acceptable acid addition salt thereof.

7. A compound as defined in claim 1, which is N-(1-ethyl-4-piperidyl)-2-(8-trifluoromethyl-4-quinolylamino)benzamide or a pharmaceutically acceptable acid addition salt thereof.

8. A compound as defined in claim 1, which is 2-(9-chloro-4-quinolylamino)-N-(1-ethyl-3-piperidyl) benzamide or a pharmaceutically acceptable acid addition salt thereof.

9. A compound as defined in claim 1, which is 2-(8-chloro-4-quinolylamino)-N-(2-diethylaminoethyl)-N-ethylbenzamide or a pharmaceutically acceptable acid addition salt thereof.

10. A pharmaceutical composition useful as an analgesic comprising a pharmaceutically acceptable carrier and an active amount of a compound having the formula:

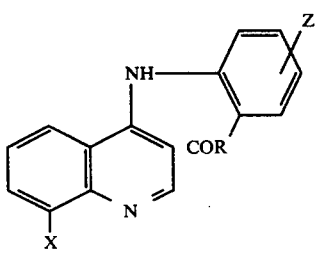

or a pharmaceutically acceptable acid addition salt thereof, wherein X is selected from trifluoromethyl and halogen, Z is selected from hydrogen, halogen, lower alkyl, lower alkoxy, nitro, di(lower alkyl) amino and trifluoromethyl and R is selected from the groups having the formulae

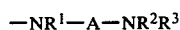

and

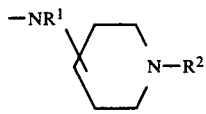

where $R^1$ is selected from hydrogen and lower alkyl, $R^2$ is lower alkyl, $R^3$ is lower alkyl and A is lower alkylene.

11. An analgesic composition as defined in claim 10 in the form of a tablet or capsule.

12. A method of providing analgesia in a mammal in need thereof, which comprises administering to said mammal an analgesic effective dose of a pharmaceutical composition comprising a pharmaceutical acceptable carrier and an active amount of a compound having the formula:

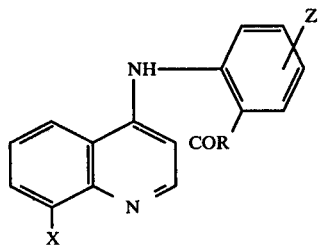

or a pharmaceutically acceptable acid addition salt thereof, wherein X is selected from trifluoromethyl and halogen, Z is selected from hydrogen, halogen, lower alkyl, lower alkoxy, nitro, di(lower alkyl) amino and trifluoromethyl and R is selected from the groups having the formulae

and

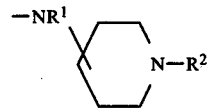

where $R^1$ is selected from hydrogen and lower alkyl, $R^2$ is lower alkyl, $R^3$ is lower alkyl and A is lower alkylene.

13. A method of providing analgesia in a mammal in need thereof, which comprises administering to said mammal an analgesic effective dose of a pharmaceutical composition comprising a pharmaceutically acceptable carrier and an active amount of a compound selected from the group consisting of N-(1-ethyl-3-piperidyl-2-(8-trifluoromethyl-4-quinolylamino)benzamide, N-(2-diethylaminoethyl)-N-ethyl-2-(8-trifluoromethyl-4-quinolylamino)benzamide, N-(1-ethyl-4-piperidyl)-2-(8-trifluoromethyl-4-quinolylamino)benzamide and 2-(8-chloro-4-quinolylamino)-N-(2-diethylaminoethyl)-N-ethylbenzamide or a pharmaceutical acceptable acid addition salt thereof.

* * * * *